United States Patent
Wiesmann et al.

(10) Patent No.: US 6,519,485 B2
(45) Date of Patent: Feb. 11, 2003

(54) MINIMALLY INVASIVE SYSTEM FOR ASSESSMENT OF ORGAN FUNCTION

(75) Inventors: William P. Wiesmann, Washington, DC (US); Adrian Richard Urias, Germantown, MD (US); Jill Uyeno, Mission Viejo, CA (US); Adrian Prokop, Seattle, WA (US); Jason Milne, Eagan, MN (US); Kristopher Jarka, Sherman Oaks, CA (US); Farbod Ghassemi, Emerainville (FR)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/736,603

(22) Filed: Dec. 13, 2000

(65) Prior Publication Data

US 2002/0072661 A1 Jun. 13, 2002

(51) Int. Cl.$^7$ ............................ A61B 5/00
(52) U.S. Cl. ............. 600/328; 600/323; 600/342; 600/549
(58) Field of Search ................. 600/327, 328, 600/320, 322, 323, 309, 342, 549, 310, 339, 341; 604/19, 48, 93.01, 113, 22, 506, 19.22; 606/1, 27; 607/96, 113

(56) References Cited

U.S. PATENT DOCUMENTS 4,213,462 A * 7/1980 Sato .......................... 128/634
4,908,762 A * 3/1990 Suzuki et al. ........... 364/413.09

(List continued on next page.)

FOREIGN PATENT DOCUMENTS

WO      0028887      5/2000

OTHER PUBLICATIONS

Ghassemi et al. "Minimally Invasive System For Detecting Hepatic Shock", Final report to Center for Innovative Minimally Invasive Therapy, Boston, MA, May 15, 1999, 1998–99 Engineering Clinic, Harvey Mudd College, Claremont, CA 91711.*

Georges Delhomme et al., "Thermal Diffusion Probe and Instrument System for Tissue Blood Flow Measurements: Validation in Phantoms and In Vivo Organs" (*IEE Transactions on Biomedical Engineering*) (Jul. 1994) vol. 41, No. 7, pp. 656–662.

Farbod Ghassemi et al., Final Report "Mimimally Invasive System for Detecting Hepatic Shock" (*Center for Innovative Minimally Invasive Therapy (CIMIT)*) (Internal Document, May 15, 1999) pp. I–XIV and 1–81.

*Primary Examiner*—Charles G. Freay
*Assistant Examiner*—Han L Liu
(74) *Attorney, Agent, or Firm*—Nutter McClennen & Fish LLP

(57) ABSTRACT

A system for assessing organ function couples light emitters into an optical fiber delivery assembly of which the tip extends to or into an internal organ and illuminates tissue; the device senses temperature at the tip, and a collection fiber collects light scattered, reflected or emitted by the surrounding tissue. Control and processing modules drive the laser diodes and process return spectral signals, e.g., to assess metabolic activity and detect onset of shock. A prototype uses four laser diodes with peaks at 735, 760, 805 and 890 nm, with a front end splitter providing a reference beam to a photo detector for normalizing detection output and correcting the signal samples. The device may include a plurality of laser diodes and may select subsets of the sources to tailor spectral illumination to different target enzymes, metabolites or other compounds. The processor may include heuristic correlators for interpreting the physiological state or detecting the onset of shock based on magnitudes of multiple different measured parameters.

13 Claims, 4 Drawing Sheets

U.S. PATENT DOCUMENTS

| | | | |
|---|---|---|---|
| 5,127,405 A | * 7/1992 | Alcala et al. | 128/633 |
| 5,178,141 A | * 1/1993 | Kanda | 128/63 |
| 5,415,165 A | 5/1995 | Fiddian-Green | 128/632 |
| 5,456,252 A | 10/1995 | Vari et al. | 128/633 |
| 5,785,658 A | 7/1998 | Benaron et al. | 600/473 |
| 5,813,403 A | 9/1998 | Soller et al. | 128/633 |
| 6,036,654 A | * 3/2000 | Quinn et al. | 600/526 |
| 6,195,574 B1 | * 2/2001 | Kumar et al. | 600/323 |

* cited by examiner

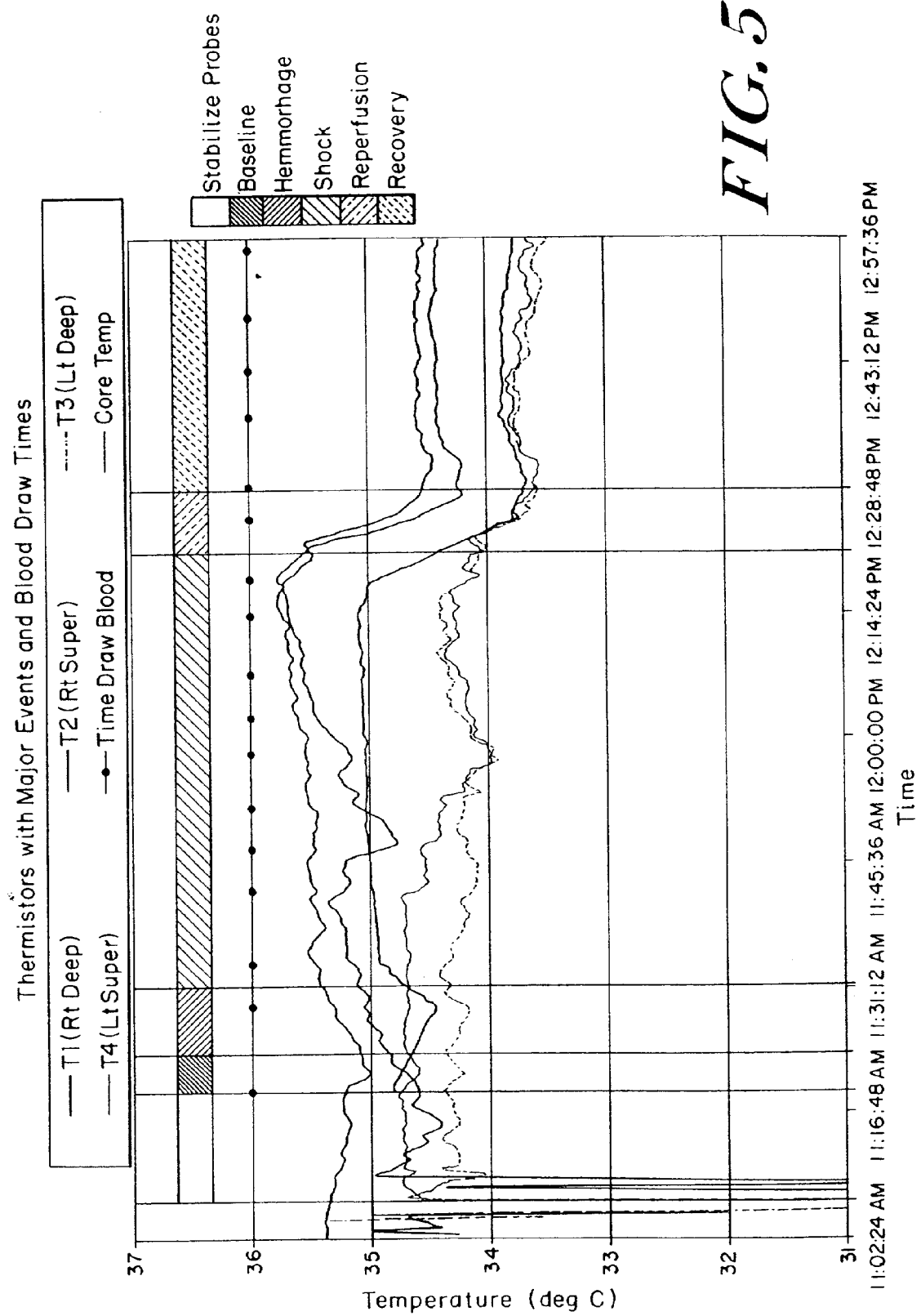

MINIMALLY INVASIVE SYSTEM FOR ASSESSMENT OF ORGAN FUNCTION

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates generally to the assessment of organ function and to the determination of critical events such as metabolic changes and pathologic responses that may occur within an organ. It is of particular utility for detecting adverse changes which generally become only slowly manifest in other anatomic systems such as blood chemistry, cardiovascular functioning or other indicators of health commonly monitored in a hospital setting.

For a critical care patient whose medical condition may change rapidly over time, constant monitoring of the body functions in real time is considered essential. Such assessment of patient condition is crucial in alerting a physician to potential problems. One serious and extremely dangerous but common problem is rapid blood loss that can induce shock. The onset of shock in critical care patients is swift, and may lead to death if not detected. Current monitoring techniques focus on vital signs such as heart rate or blood pressure, which may be inadequate to detect shock sufficiently early because these parameters do not change immediately upon onset of the underlying condition or provoking stimulus. A patient can lose ten percent or more of total blood volume before blood pressure is even affected.

Parameter changes within an organ such as the liver may be capable of providing a more immediate indication than is provided by circulating blood enzymes or other indicators, since the liver plays a key role in homeostasis. It is thus situated to provide more immediate indicia of critical changes. One might therefore hope that by monitoring parameter changes during hepatic shock, some parameters may be found to correlate with the onset of shock in a patient. If so, these might provide an early warning to allow appropriate intervention. Presently, however, liver condition is determined remotely and inferentially, primarily through blood analysis. Typically, liver function tests measure the ability of the liver to synthesize enough protein to regulate blood coagulation correctly. Although the results of such tests can be helpful, these assays generally involve a delay of hours between the onset of an adverse or trauma condition in the liver and the detection of its effects through blood analysis. After such a delay, the liver itself may already be damaged beyond repair. Thus, the development of a real-time monitoring system for the liver or other organ would greatly aid in the timely assessment of patient medical condition.

Accordingly, it is desirable to provide a method of assessing physiological organ parameters more directly.

It would also be desirable to provide a versatile and simple assay extendible to the detection of different critical parameters or conditions.

SUMMARY OF THE INVENTION

One or more of these and other desirable ends are achieved in accordance with the present invention by a system for assessing organ function wherein a plurality of light emitters of differing spectral characteristic are coupled into a fiber assembly including a percutaneous insertion and penetration body having at least one optical fiber signal guide. The percutaneous insertion body is adapted for insertion through a human body with at least its tip extending to or penetrating an internal organ so that it positions the fiber to illuminate organ tissue. A second (or the same) fiber catches light scattered, reflected or emitted by the surrounding tissue and returns a light signal to the proximal end of the device, where it is coupled to a detector. The device also senses temperature at the tip, either through an electrically connected sensing element such as a thermistor, or by a light-based technique such as infrared thermography, in which case one or more additional fibers adapted to carry a signal in the appropriate thermographic spectral region may be provided.

In a prototype embodiment, control and processing modules drive each of a plurality of laser diodes in succession to emit light in a plurality of different peak regions and at different times. This light is directed at organ tissue to interact therewith, and a detection fiber picks up and returns an interaction light signal for detection by a photo detector to determine the magnitude of each interaction signal. A beam splitter provides a portion of each of the emitted input signals as a reference signal to normalize the detected return values, which may, for example, correspond to the overall absorption in each band of specific substances selected in advance for their known occurrence during shock, or they may be simply spectral absorption values which are empirically determined to occur during organ failure, even if the specific absorbing substance remains unidentified.

In various embodiments, the instrument may assess general organ function or metabolic activity by detecting changes in light absorption attributable to one or more spectral bands characteristic of particular enzymes, proteins, metabolites or the like. In one prototype embodiment, absorption at a peak of deoxygenated hemoglobin and/or at one or more peaks of oxygenated hemoglobin may be monitored. Alternatively, relative absorption of signals on each side of a peak, or surrounding a specific wavelength, may be monitored as an indicator of organ change. Preferably a target pair of substances—biological molecules, enzymes or metabolites—are selected such that coordinated changes in different spectral regions characteristic of the pair of substances occur during shock. This allows the detection of simultaneous change in two or more distinct but associated spectral bands to be detected and more dependably correlated as an indicator of condition. The detection processing may include a time-varying detection protocol which may, for example enhance detection of a blood-flow related substance. In one embodiment, the device performs a relative discrimination of state by monitoring pulse oxygen saturation of hemoglobin in real time together with one or more other parameters such as temperature. A correlation of changes in the different monitored parameters then serves as a warning indicator of organ failure.

As applied to a prototype monitor embodiment for detecting change correlated to shock in the liver, a prototype for a body-insertable device employed four different laser diodes having peaks at 735, 760, 805 and 890 nm, and connected to a common optical fiber. The diodes were driven at output powers between about 50 to 100 mW to illuminate organ tissue, and a front-end splitter separated a portion of the beam as a reference beam that was directed to a photo detector to develop an input power signal used to normalize the level of the detection output from the return fiber.

Suitable coupling for the input light signal may be obtained by collimating and focusing each diode output into a bundle whose output is then directed into the delivery fiber, or may be fabricated by fusing pairs of two hundred micrometer core diameter multimode fibers with an SMA connector as an end coupler. The return fiber for collecting an interaction signal consisting of the light collected from or through the organ tissue and returning it to the photo detector may have a collection face (such as a bevel) or a light-gathering pipe, oriented to avoid catching direct illumination. The photo detector may be a broad band detector useful over a range, for example, of 320 to 1100 nanometers. Preferably high sensitivity detectors with a detection threshold of a milliwatt or less are employed. In various embodiments, the system may be used in an absorbance, reflectance or fluorescence mode and may perform detection after filtering the input and/or return signal with one or more narrow band filters and/or band pass or cut-off filters to allow use of lesser quality light sources, or to tailor the applied or return narrow band probe wavelengths for detection of particular materials.

A physical implementation of the percutaneous monitor instrument of the present invention may be configured for catheter insertion, or may be implemented as a semi-rigid assembly having its fibers, and electrical connections if present, carried within a metal piercing sleeve that is itself capable of penetration and insertion directly through the skin and into an organ. Preferably, a control module such as a programmed microprocessor, allows the user to adjust data acquisition parameters and to view in real time the output signals as well as the measured or calculated parameters corresponding to those signals. The control module may also control the underlying signal acquisition, e.g., firing sequence and ON times of laser diodes, timing of return light signal sampling measurements, and size of samples and data stores, to optimize the capture of a meaningful measurement. In other embodiments, the instrument may be configured with a larger plurality of light sources of which only a portion are illuminated for each assay. Specific narrow band diodes may be provided effective to excite particular spectral responses or detect highly characteristic absorbances, or the diodes may collectively cover a broad spectral region with numerous smaller spectral bands. For such an instrument; the selection of particular diodes may be varied for different assays to tailor the spectral illumination to detection of a different specific intended target substances or organ conditions. The processor may include heuristic correlators or programmed interpretations and displays for indicating the physiological state based on measured magnitudes of the multiple different detected signals.

BRIEF DESCRIPTION OF THE DRAWINGS

These and other features of the invention will be understood from the description below taken together with drawings of details of operation and construction of illustrative embodiments, wherein:

FIG. 5 show temperature correlation with organ condition for plural liver sites.

DETAILED DESCRIPTION

Figure 1:
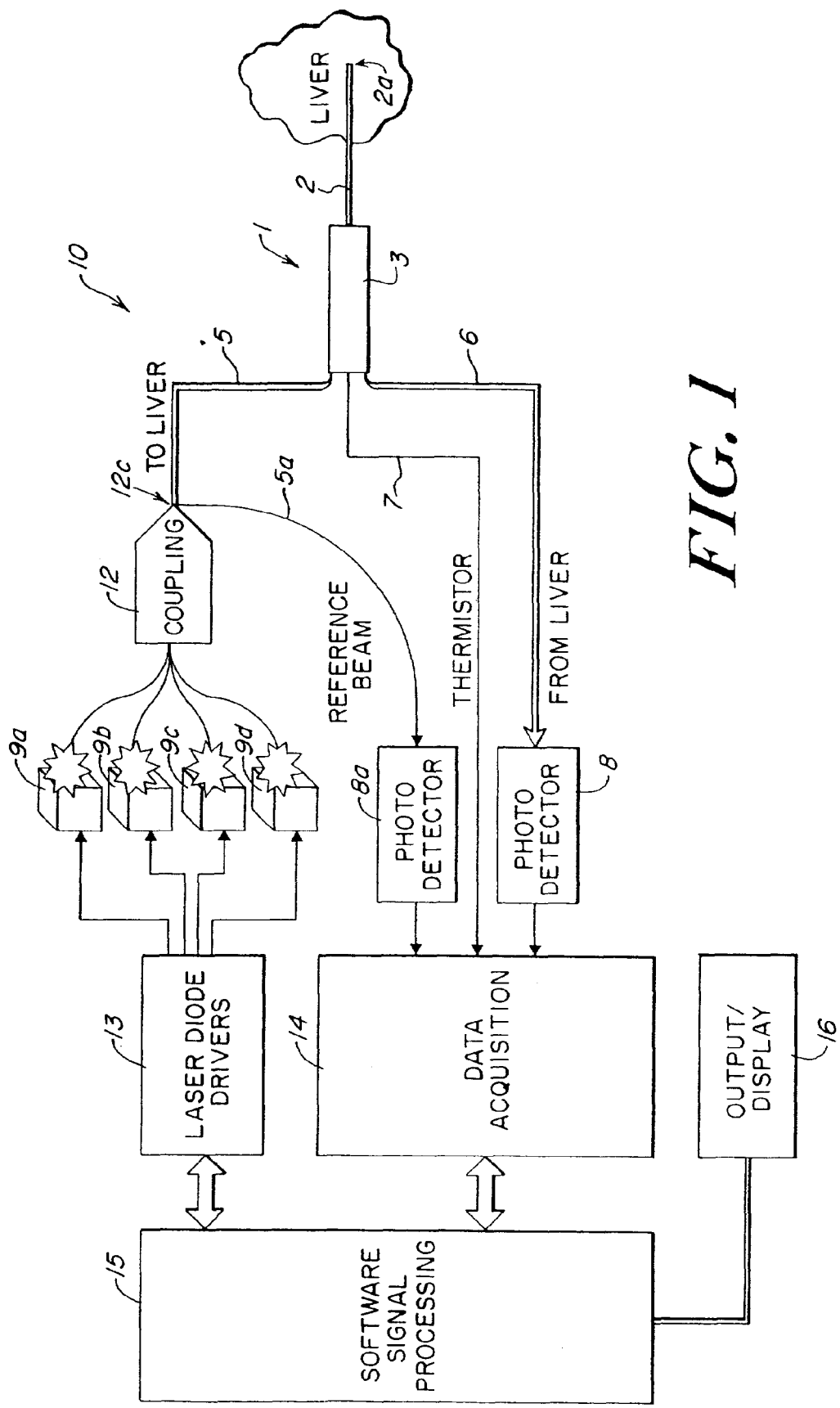
FIG. 1 illustrates an organ function assessment device of the present invention.

FIG. 1 illustrates in schema an organ function monitoring or assessment system 10 in accordance with the present invention. As shown, the system includes a probe 1 having a junction or handle portion 3 and an elongated needle-like or catheter-like body 2 adapted to position a tip region 2a of the body in or proximate to the tissue of an internal organ of a living body. FIG. 1 schematically shows the tip 2a penetrating a liver. The elongated portion 2 may, for example, be formed with a metal sheath or tube of suitable diameter, which as described further below, may be configured for insertion via a cannula, or the tip may be directly insertable through tissue to penetrate the target organ, so that the tip region is intimately surrounded by the target tissue. While not illustrated, the invention also contemplates that the probe portion may be implemented with a short penetrating tip assembly that is deployed endovascularly and then extended and inserted into target tissue from the tip of a catheter delivery device. The tip shape, sharpness and tube profile and outer diameter are such that the piercing tip may enter the organ and may be withdrawn with little or no bleeding or trauma.

As further shown in FIG. 1, the probe 1 connects with signal lines 5, 6, 7 for applying signals to and detecting signals from the tip 2a. In this embodiment, signal lines 5 and 6 are optical fibers; line 5 carries a light signal to the tip, and line 6 returns a portion of that signal which has interacted with surrounding tissue to a photo detector 8. A portion of the signal traveling in or provided to fiber 5 is also initially split off and passes along fiber 5a to photo detector 8a to develop a measure of the input intensity or signal power. The photo detector 8a may be a separate detector, may be the same as photo detector 8, or may be a separate detection region fabricated on a common chip with photo detector 8 so as to have essentially identical response characteristics. The signal line 7, the third signal line connected to the handle 3, is an electrical signal line, and in this embodiment it connects to a thermistor (not shown) located at the tip of the elongated probe 2 and positioned to register the temperature of the region that is optically probed by the light signal provided on line 5. Thus, the probe is adapted to gather spectral response information simultaneously with the additional information provided along line 7 from a small region of the organ.

As further shown in FIG. 1, a plurality of different laser diodes 9a, 9b, 9c, 9d are coupled via a coupling assembly 12 into the fibers 5, 5a. The coupling assembly 12 may be a commercially available multi-fiber coupling device, that may also include a split-off port 12a connected to the fiber 5a, which splits off a portion of the signal being coupled as an output beam into the output fiber 5. Diode beam combining and output splitting may alternatvely be effected by a coupling fabricated, for example, by appropriate fusing and coupling together into a single output fiber of the successive diode output fibers extending from the individual laser diodes 9a, 9b. . . , and fusing/coupling the output fiber with the fiber 5a to split the illumination signal. A laser diode driver unit 13 drives the laser diodes, while a data acquisition module 14 receives output detection signals from the photo detector output and from the thermistor signal line 7 of the probe. The driver unit 13 may have drive circuitry of an appropriate power level for powering the laser diodes in response to on/off signals provided at an input, while the data acquisition unit 14 may include such circuitry as a preamplifier and signal digitizer for digitizing and storing the photo detector signal line outputs. The data acquisition module may also include suitable circuitry such as a suitable driver or bridge detection circuit and A/D conversion or the like to provide a temperature-dependent digitized voltage output from the electrical temperature sensing element or thermistor signal on line 7.

The data acquisition unit may be implemented in a straightforward manner with a microprocessor programmed to sample and store the various electrical outputs at times associated with the diode drive intervals, and to implement registers or other storage configured to receive an ordered set of measurement data—i.e., the digitized thermistor and photo detector output data—to implement the determinations described below. The units 13, 14 may each be controlled by a common microprocessor which also preferably implements the signal storage registers and the software signal processing for interpretation of the data samples acquired by unit 14.

In the illustrated system, the interpreted data or final output, as discussed further below, may involve displaying a measurement value, a waveform, or an alarm warning. The quantitative results or interpretive data are displayed on output display, 16 which may, for example, include a printer, a monitor or various sorts of alarms.

As discussed in more detail below, the different laser diodes are selected so that individually or together, the extent of their absorption by liver tissue provides an indication of one or more metabolic states or events in real time. To this end each laser diode is separately driven for a brief time interval and its light is coupled into and along fiber 5 to the tip where it is directed at the organ being monitored. The tip of fiber 6 is positioned to receive light which has been scattered in passing through the organ tissue due to its statistical interactions with the cells and substances of that tissue along an interaction path that may, for example have a mean path length of about one-half to about ten millimeters. The emission and collection regions of fibers 5 and 6, respectively, may be shaped, treated and positioned to efficiently maximize the desired signal. Thus, for example, the receiving fiber may be positioned to receive a scattered glow from tissue, without permitting a direct path from fiber 5 to fiber 6. Thus, illustratively, the received signal may consist of attenuated light of the applied signal.

Return light along fiber 6 is provided to the photo detector 8, the output of which is sampled and stored. In a representative illumination procedure, the diodes may each be driven in succession for a time interval of five or ten milliseconds, while the light collected in fiber 6 is passed to the photo detector, whose output is monitored during a corresponding sampling period for detecting the magnitude of the return signal.

In a prototype embodiment configured to detect spectral absorption, the laser driving and return signal sampling are performed simultaneously. A dark period, which may also be of five or ten milliseconds duration, follows each illumination period, and preferably the photo detector dark current is measured in this period and the dark value, as detected by detectors 8 and 8a, is subtracted from each of the return and reference values, respectively, to normalize the sampled photo detector output return and reference signals. In other embodiments where the desired assay involves stimulating a fluorescence or phosphorescence effect with the diode illumination from fiber 5, the two operations of illumination and detection may be carried out with only partial overlap, or may be performed successively in disjoint time intervals. In such cases the overlap or lag between illumination and sampling is selected so as to enhance signal collection, e.g., so that the return signal maximizes detection of persistent phosphorescence, or so that all or a portion of the return signal detection is performed during the dark time when no laser diode is on. In the latter case, a fixed delay may be provided between the onset or the termination of a signal in line 5 and the onset or termination of detector sampling on line 6, and the detection of dark current may be shifted to before the input pulse to avoid contamination by the tissue response.

In each case, a portion of the applied input laser signal is split off by a beam splitter and passed to photo detector 8a, and this measurement is used to scale or normalize the return signal from line 6. The beam splitter may be a broad band splitter, such as a partially silvered (e.g., ten to twenty per cent reflective) mirror, or a 1:10 fiber splitting junction, or other splitting arrangement. The microprocessor controller may be a simple PC, and the data acquisition module 14 may be implemented using a data acquisition card in the PC that receives suitably digitized and conditioned return signals. Similarly, the laser diode driver unit 13 may be controlled by the PC with software that sets the multiplexing times and durations, magnitude of drive current and the like for producing the laser diode optical probe signals being sent into the liver and collecting the optical return signals.

Prior to feasibility testing, applicant determined a range of available components and did preliminary modeling of signal parameters. Based on the sensitivity of a selected photo detector that was about $5 \times 10^{-11}$ watts for detection of a return signal of four milliseconds duration, and assuming a measurement arrangement wherein light from the input fiber diffuses into and through tissue for several millimeters before entering the collection fiber, applicant calculated a minimum necessary input signal power. The in vitro attenuation coefficient $\alpha$ and the effective penetration depth were first determined for a range of wavelengths between .4 and 1.0 micrometers for pig liver tissue and for human liver tissue. A set of four probe wavelengths were then selected for a prototype implementation discussed further below, based on one intended assay, a hemoglobin oxygenation model, and the effective penetration depths for these specific wavelengths were interpolated, after which a minimum initial driver intensity was calculated based on the wavelength with the lowest penetration depth. Assuming a five millimeter tissue interaction path between the input and collection fibers, the required input intensities were calculated to be about $7 \times 10^{-10}$W for the porcine model, and $6 \times 10^{-8}$W for human liver. Corresponding input requirements for a 10 mm interaction length were $7.4 \times 10^{-9}$W and $5.6 \times 10^{-5}$W, respectively.

Figure 2:
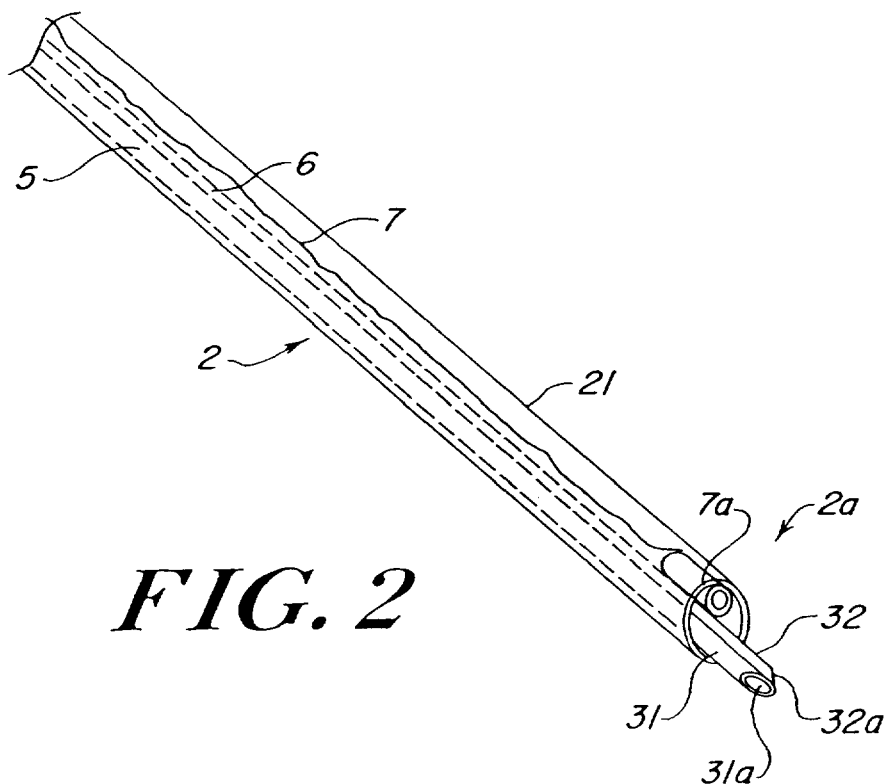
FIG. 2 illustrates an alternative embodiment of a device of the present invention.

The prototype system employed four 1:2 branched optical couplers, obtained from Ocean Optics, to couple the four source diodes into a single fiber, and then to split this signal into two branches for coupling into the probe fiber 5 (FIG. 1) and reference fiber 5a, respectively. Maximum light transmission was about 12.5%, with the probe and reference signals being about equal. PDA55 photo detectors from Thorlabs, having a detection range over 320–1100 nm were used. The probe apparatus employed two 200 micrometer core multimode optical fibers 31, 32 as the input and collection fibers. These had their tips 31a, 32a cut at 45° to the normal, in a configuration shown in FIG. 2, and were placed in an elongated probe tip body 21 having the size of a 3 French catheter. The cut faces 31a, 32a were angled away from each other so as to shield the collection fiber from direct illumination by the input fiber. This geometry thus defined the illuminated tissue interaction region and determined the mean light-tissue interaction path length to get an effective measurement signal. The 45° fiber tip angle also provided a sharp but hardy penetrating point structure for light path engagement with the target organ. A more, or a less, acutely-sloped end face angle could be chosen so as to change the total interaction volume and obtain expected interaction light paths P having a different level of tissue modulation of the collected light. A thermistor 7a is shown mounted within the probe tip 2a and connected to the circuit line(s) 7. As shown, thermistor 7 is essentially positioned at the fiber light detection region. However, the fiber ends may project beyond the thermistor so as to more readily be urged against or immersed in organ tissue. The probe tip may in some embodiments employ a robust placement structure, such as a retractable penetrator/shield, or may utilize a catheter or cannula delivery structure, to assure effective placement or use without requiring the light delivery tip structure to bear structural or penetrating stresses. Furthermore, in other embodiments, the two fibers 31, 32 need not be the ultimate illumination and collection faces. Instead, the fibers may connect to separate light pipes, or to specially shaped guiding illuminator/collector bodies at their tips to enhance tip strength, or optimize tissue interaction volume or path length.

Figure 3:
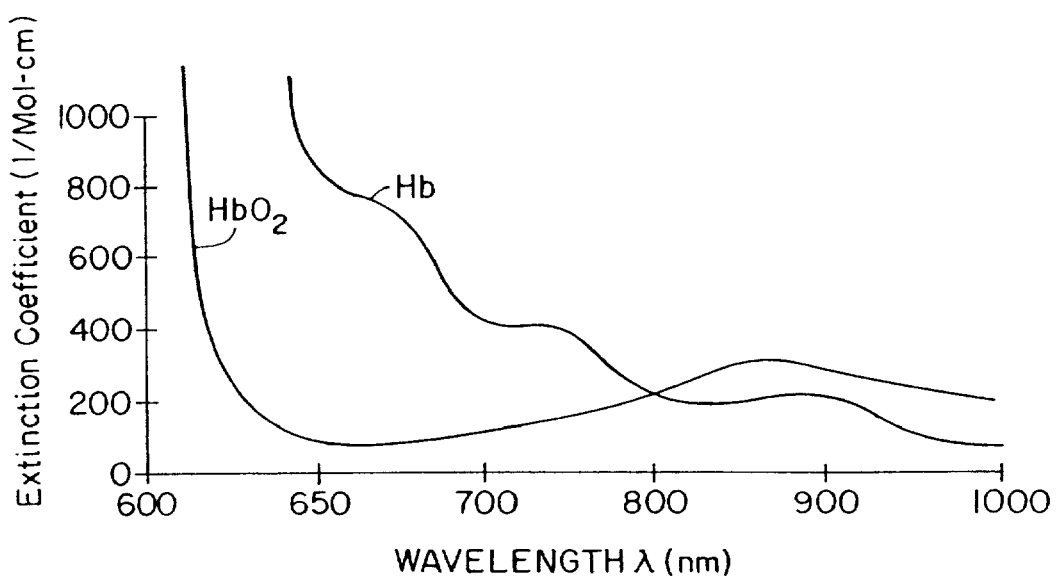
FIG. 3 illustrates steps in a method of the present invention.

As noted above, the laser diode wavelengths were chosen in the prototype embodiment to monitor blood oxygenation, or more specifically, to discriminate the relative amounts of oxygenated hemoglobin and deoxygenated hemoglobin present in the targeted organ tissue. FIG. 3 illustrates the extinction coefficient of oxygenated and de-oxygenated hemoglobin as a function of wavelength. As shown, the curves have opposite slopes and cross at about 800 nm. Applicant set about to implement a simple test for metabolic level by assessing absorption at several wavelengths in bands adjacent to 800 nm, or in the region 650–750 nm where deoxygenated hemoglobin is highly absorbing.

In the prototype embodiment, four laser diodes having peaks at 735 nm, 760 nm, 805 nm and 890 nm were employed. Each diode was coupled through a different filter that further narrowed the band width of the diode output signal, and the diodes were fired successively, leaving a dark phase between firings. Signal levels were sampled from the fiber 5a and the collection fiber during each illumination, and the entire cycle of illumination and sampling was performed approximately thirty times per second. Temperature readings were also taken, and the detected values were processed to assess organ function. During the time that each laser diode was ON, one signal value from both the reference and sensing photo detectors was acquired. The corresponding dark phase value recorded in that cycle was subtracted from the acquired signal data, which was then normalized by dividing the return fiber measurement photo detector output by a scaled reference fiber photo detector output.

Figure 4:
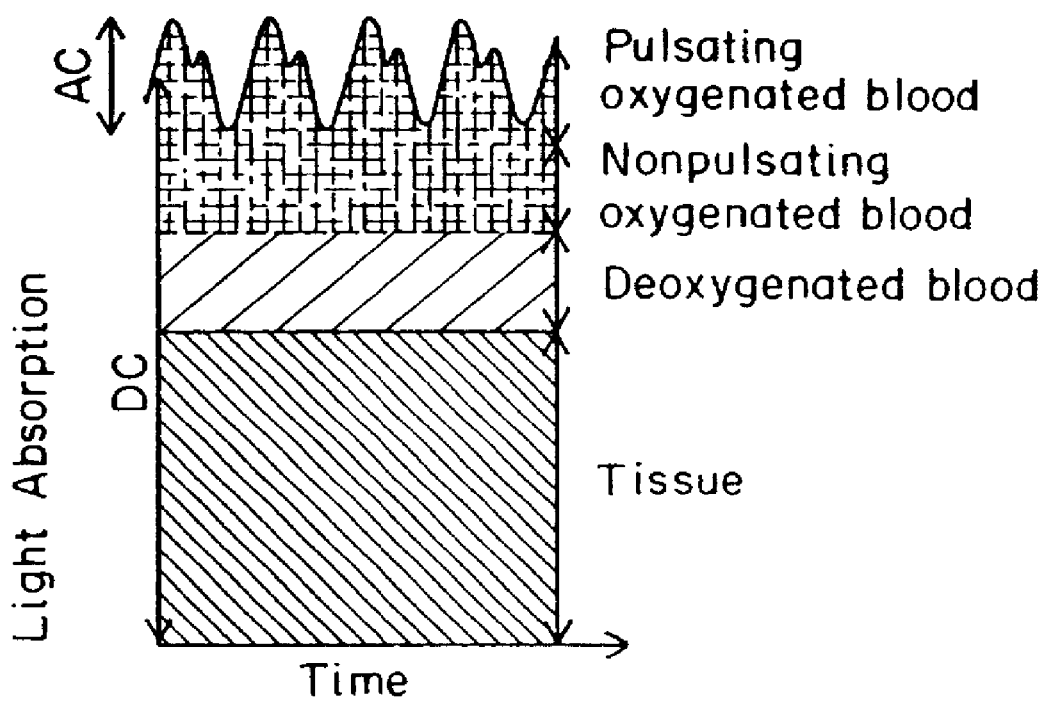
FIG. 4 illustrates pulse oxymetry measurement and components thereof.

The resulting measurements provide data on the absorbance at a plurality of wavelengths distributed over a broad band, and the numerical signal readings may be combined in different combinations to track relevant physiological indicators. For example, the breakdown of sugar in the liver requires oxygen, so monitoring oxygen saturation provides an indication of oxygen consumption, hence of liver functionality. This may be assessed by combining the repeated absorption measurements to obtain a pulse oximetry output as shown in FIG. 4. In proof of principle experiments to assess the efficacy of these measures, shock was induced in an animal while monitoring liver temperature, spectral data, and pulse oxygen saturation. FIG. 5 shows the measured temperature at a plurality of sites in the liver during the course of hemmorhage, shock, reperfusion and recovery. The onset of shock was associated with an increase in temperature and a decrease in pulse oxygen saturation, with an increase in deoxygenated blood, which was confirmed by the DC level of a conventional pulse oxymeter. Thus several correlated changes provided dependable indications of shock using a minimally invasive spectral/thermal probe strategy.

The invention being thus disclosed and illustrative embodiments depicted herein, further variations and modifications of the invention will occur to those skilled in the art, and all such variations and modifications are considered to be within the scope of the invention, as defined by the claims appended hereto and equivalents thereof.

What is claimed is:

1. A system for monitoring the function of an organ in a patient, wherein the organ contains one or more target substances, each having a characteristic spectral band, such system comprising:
   a detecting component, disposed within a probe having a tissue-penetrating tip, for collecting data relating to a plurality of physiological parameters of the organ, wherein the probe is configured for insertion into the organ and the detecting component is adapted to collect said plurality of data parameters simultaneously so as to detect in real time correlated changes of the characteristic spectral band of each of the one or more target substances to determine physiological parameters indicative of onset of shock.

2. The system of claim 1, wherein the detection component includes a light delivery conduit for illuminating and collecting return light from a plurality of discrete spectral sources to monitor the spectral characteristics of target substances within the organ.

3. The system of claim 1, wherein the detecting component comprises a plurality of fiber-optics and photo detectors.

4. The system of claim 3, wherein the detecting component further comprises a plurality of laser diodes.

5. The system of claim 1, wherein the detecting component further comprises a temperature sensor.

6. The system of claim 6, wherein the physiological parameters include at least one of organ temperature and organ level of deoxygenated hemoglobin.

7. A device for monitoring at least two physiological parameters associated with an organ, comprising:
   a catheter having a proximal end, a tissue-penetrating distal end adapted to be inserted into tissue of the organ, and a housing extending between the proximal end and the distal end, the housing defining a catheter lumen, wherein the catheter is effective to detect temperature at the distal end of the catheter; and
   a fiber-optic element extending through the catheter lumen from the proximal end to the distal end of the catheter and being adapted to emit light to the organ tissue and to receive reflected light from the organ tissue, the reflected light being effective to generate data regarding a level of oxygenated hemoglobin associated with the organ.

8. The device of claim 7, further comprising a temperature sensor disposed proximate the distal end of the catheter.

9. A method for assessing the functionality of an organ in real-time, comprising the steps of:
   inserting a catheter for collecting data from the organ to a location inside the organ, the catheter having a proximal end, a tissue-penetrating distal end and a housing extending between the proximal end and the distal end, the housing having disposed therein a plurality of fiber-optics and a thermistor for detecting temperature at the distal end of the catheter;

transmitting light to the organ and receiving reflected light from the organ, the light being transmitted along the plurality of fiber-optics and being effective to generate data regarding a level of hemoglobin deoxygenation associated with the organ;

receiving data collected by the catheter, the data reflecting the level of hemoglobin deoxygenation and temperature associated with the organ; and interpreting the data to generate a real-time indicator of the functionality of the organ.

10. A system for monitoring the function of an organ in a patient, wherein the organ contains one or more target substances, each having a characteristic spectral band, such system comprising:

a probe having a proximal end and a tissue-penetrating distal end adapted to be inserted into the organ; and a detecting component disposed within the probe for collecting data relating to physiological parameters of the organ, wherein said detecting component includes an optical fiber transmission means for relaying light between the proximal and the distal ends of the catheter, wherein the detecting component determines correlated changes of the characteristic spectral band of each of the one.or more target substances in the organ to provide an effective parameter indicator for the onset of shock.

11. The system of claim 10, wherein the effective parameter indicator includes a spectral parameter indicator of hemoglobin deoxygenation.

12. The system of claim 11, wherein the effective parameter indicator includes a temperature indicator.

13. The system of claim 10, wherein the detecting component is adapted to assess liver function by detecting correlated changes of the characteristic spectral band of each of the one or more target substances associated with liver function, and said effective parameter indicator includes a composite indicator of liver metabolic activity.

* * * * *

UNITED STATES PATENT AND TRADEMARK OFFICE
CERTIFICATE OF CORRECTION

| | | |
|---|---|---|
| PATENT NO. | : 6,519,485 B2 | Page 1 of 1 |
| APPLICATION NO. | : 09/736603 | |
| DATED | : February 11, 2003 | |
| INVENTOR(S) | : William Wiesmann et al. | |

It is certified that error appears in the above-identified patent and that said Letters Patent is hereby corrected as shown below:

At column 1, line 5, before "BACKGROUND OF THE INVENTION", insert the following:

--STATEMENT REGARDING FEDERALLY SPONSORED RESEARCH

This invention was made with Government support under Grant No. DADMD17-99-2-9001 awarded by the U.S. Department of the Army. The U.S. Government has certain rights in this invention.--

Signed and Sealed this

Seventh Day of July, 2009

JOHN DOLL
*Acting Director of the United States Patent and Trademark Office*